United States Patent
MacLaughlin

(10) Patent No.: US 11,166,695 B2
(45) Date of Patent: Nov. 9, 2021

(54) LEARNING SYSTEM AND METHOD FOR MOBILE RADIOGRAPHY POWER MANAGEMENT

(71) Applicant: Carestream Health, Inc., Rochester, NY (US)

(72) Inventor: Scott T. MacLaughlin, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 442 days.

(21) Appl. No.: 15/948,110

(22) Filed: Apr. 9, 2018

(65) Prior Publication Data

US 2019/0307413 A1    Oct. 10, 2019

(51) Int. Cl.
  *A61B 6/00*    (2006.01)
  *G06N 3/08*    (2006.01)

(52) U.S. Cl.
  CPC ............ *A61B 6/56* (2013.01); *A61B 6/4405* (2013.01); *A61B 6/563* (2013.01); *G06N 3/08* (2013.01)

(58) Field of Classification Search
  CPC ......... A61B 6/4405; A61B 6/56; A61B 6/563; H02J 9/061; H02J 9/062; G06N 3/08
  See application file for complete search history.

(56) References Cited

U.S. PATENT DOCUMENTS

| | | | | |
|---|---|---|---|---|
| 5,594,345 A * | 1/1997 | Boehm | ............... | A61B 6/4405 320/132 |
| 10,010,305 B2 * | 7/2018 | Tsuyuki | ............... | A61B 6/56 |
| 2005/0047551 A1 * | 3/2005 | Dong | ............... | H05G 1/265 378/204 |
| 2006/0181243 A1 * | 8/2006 | Graves | ............... | G16H 40/20 320/116 |
| 2008/0104421 A1 * | 5/2008 | May | ............... | G06F 1/3203 713/300 |
| 2008/0170666 A1 * | 7/2008 | Coombs | ............... | A61B 6/56 378/101 |
| 2008/0201587 A1 * | 8/2008 | Lee | ............... | G06F 1/329 713/320 |
| 2010/0010857 A1 * | 1/2010 | Fadell | ............... | G06Q 10/0639 705/7.38 |
| 2011/0110498 A1 * | 5/2011 | Takae | ............... | G01R 31/36 378/102 |
| 2011/0186741 A1 * | 8/2011 | Ohta | ............... | A61B 6/42 250/370.08 |
| 2011/0238343 A1 * | 9/2011 | Kamiya | ............... | G01R 31/392 702/63 |
| 2011/0252247 A1 * | 10/2011 | Yokoyama | ............... | H02J 9/061 713/300 |
| 2011/0317809 A1 * | 12/2011 | Eguchi | ............... | A61B 6/4494 378/62 |
| 2012/0033783 A1 * | 2/2012 | Katayama | ............... | G16H 30/20 378/19 |

(Continued)

*Primary Examiner* — Dani Fox
*Assistant Examiner* — Soorena Kefayati

(57) ABSTRACT

A power consumption rate of a battery is monitored according to time of day and is recorded as a battery power consumption profile associated with a plurality of daily time periods for that battery. Electric circuits connected to the battery are activated during high battery power consumption rate time periods and deactivated during low battery power consumption rate time periods. A stored control program is executable by a processor to control the automatic power downs and power ups.

13 Claims, 7 Drawing Sheets

(56) References Cited

U.S. PATENT DOCUMENTS

| | | | |
|---|---|---|---|
| 2012/0122526 A1* | 5/2012 | Bockus | H04W 52/0258 455/572 |
| 2012/0162692 A1* | 6/2012 | Aida | G06K 15/4055 358/1.14 |
| 2012/0210325 A1* | 8/2012 | de Lind van Wijngaarden | G06F 1/329 718/103 |
| 2012/0256099 A1* | 10/2012 | Gregerson | A61B 6/035 250/453.11 |
| 2012/0315960 A1* | 12/2012 | Kim | H04M 1/72448 455/574 |
| 2013/0039473 A1* | 2/2013 | Kojima | A61B 6/547 378/91 |
| 2013/0135659 A1* | 5/2013 | Ebi | G06K 15/4055 358/1.14 |
| 2013/0138983 A1* | 5/2013 | Geary | H04W 52/0254 713/320 |
| 2013/0262891 A1* | 10/2013 | Gudlavenkatasiva | G06F 1/3212 713/320 |
| 2013/0274942 A1* | 10/2013 | Rees | H02J 13/00026 700/295 |
| 2014/0075222 A1* | 3/2014 | Jackson | G06F 1/3234 713/320 |
| 2014/0181552 A1* | 6/2014 | Andreoli | G06F 3/126 713/323 |
| 2014/0215239 A1* | 7/2014 | Kovatchev | H04W 52/0264 713/320 |
| 2014/0334597 A1* | 11/2014 | Tsuyuki | A61B 6/54 378/4 |
| 2015/0085969 A1* | 3/2015 | Mekonnen | A61B 6/56 378/4 |
| 2015/0145483 A1* | 5/2015 | Shinohara | H02J 7/0071 320/134 |
| 2015/0201899 A1* | 7/2015 | Uchinomiya | G16H 30/20 378/62 |
| 2015/0223767 A1* | 8/2015 | Sehnert | A61B 6/06 378/42 |
| 2015/0271904 A1* | 9/2015 | Heidinger | A61B 6/56 378/112 |
| 2015/0312999 A1* | 10/2015 | Takahashi | H05G 1/32 378/92 |
| 2015/0346933 A1* | 12/2015 | Vyas | G06F 3/0484 715/772 |
| 2017/0000429 A1* | 1/2017 | Nose | B60B 37/04 |
| 2017/0020480 A1* | 1/2017 | Hishikawa | A61B 6/4405 |
| 2017/0085122 A1* | 3/2017 | Nasiri | H02J 9/061 |
| 2017/0281116 A1* | 10/2017 | Hishida | A61B 6/56 |
| 2017/0285119 A1* | 10/2017 | Kanakasabai | G01R 33/3614 |
| 2018/0035524 A1* | 2/2018 | Matsuura | A61B 6/56 |
| 2018/0041626 A1* | 2/2018 | Dods | H04M 11/00 |
| 2018/0081417 A1* | 3/2018 | Chan | G06F 1/329 |
| 2018/0088959 A1* | 3/2018 | Bailey | G06F 9/4418 |
| 2018/0116625 A1* | 5/2018 | Kim | A61B 6/4405 |
| 2018/0263591 A1* | 9/2018 | Shanthakumar | H02J 7/0047 |
| 2019/0015066 A1* | 1/2019 | Kim | H01M 10/488 |
| 2019/0044336 A1* | 2/2019 | Wagner | H02J 3/32 |
| 2019/0104603 A1* | 4/2019 | Boehm | A61B 6/4405 |
| 2019/0171262 A1* | 6/2019 | Ghosh | G06F 1/329 |
| 2019/0305383 A1* | 10/2019 | Muntes | G06F 1/3296 |
| 2021/0013554 A1* | 1/2021 | Proebstle | H02J 7/14 |

\* cited by examiner

LEARNING SYSTEM AND METHOD FOR MOBILE RADIOGRAPHY POWER MANAGEMENT

FIELD OF THE INVENTION

The invention relates generally to the field of mobile medical radiography imaging and more particularly to systems and methods for management of battery power resources therefor.

BACKGROUND

Mobile x-ray systems are of particular value in intensive care unit (ICU) and other patient care environments where timely acquisition of a radiographic image is important. Because it can be wheeled around the ICU or other hospital area and brought directly to the patient's bedside, a mobile x-ray system allows an attending physician or clinician to have recent information on the condition of a patient and helps to reduce the risks entailed in moving patients to stationary equipment in a radiological imaging department.

The perspective view of FIG. 1 shows an example of a mobile radiography system 60 that can be employed for computed radiography (CR) and/or digital radiography (DR). A mobile radiography system 60 on wheels 64 enables transporting the mobile radiography system 60 by rolling. A base frame 62 includes a display 61 for display of captured radiographic images, an interactive graphical user interface, and alphanumeric data. A control panel 74 allows data input by an operator, such as via a keyboard, and selective operator control of the mobile radiography system 60. The operator may use the control panel 74 to control firing of an x-ray source 68 as well as related functions such as storing, transmitting, modifying, and printing of an obtained radiographic image.

One or more DR detectors 69 may be inserted into a slot 70 in the base frame 62 to be carried the mobile radiography system 60 during transport and may be connected to a recharging system therein when not used for radiographic imaging. A central processing system 72 provides an electronic control system that executes programmed logic functions for the mobile radiography system 60, including control of mobile radiography system 60 movement and positioning of an x-ray head 67 having an x-ray source 68 therein with an attached collimator (not shown), which x-ray head 67 may be attached to an adjustable column 66. The electronic control provided by processing system 72 is in signal communication with the x-ray head 67 for controlling actuation and firing of the x-ray source 68 therein.

Mobile radiography system 60 has an internal battery 80 or other self-contained power source disposed within or coupled to frame 62 and used to power various components of the mobile radiography system 60, including a transport drive system 76 with motors mechanically connected to drive the wheels 64 for facilitating rolling movement of the mobile radiography system 60 to different sections or departments within a medical facility. The processing system 72 may include dedicated logic processors for controlling various functions and displays, provide operator interface utilities and display imaging results, control wireless transmitters and detectors 69, adjustable columns and other positioning facilities, including collimator lights, the x-ray source 68, and other functions. A handle 58 provides for steering control of the mobile radiography system 60.

Typically, battery 80 is provided as a bank of multiple battery cells, such as lead-acid batteries. These power storage sources are heavy, expensive, and can take up appreciable space within frame 62. Efficient management of battery resources and power consumption can help to reduce power requirements and consequently to reduce the number of batteries needed, their size, and weight. Weight reduction is particularly advantageous, since typical lead-acid batteries can be relatively heavy. The weight of the batteries necessitates a higher power drive system for the cart, which further increases weight, cost, and overall complexity.

When the mobile radiography system 60 runs low on power, it is removed from service for recharging, such as coupling the battery 80 to a wall socket. This downtime is costly and expensive. Any disruption and delay that results from recharging, replacing or reloading power sources for the mobile radiography system 60 can compromise the ability of practitioners to provide portable imaging services promptly and effectively in hospital and general clinical environments. Solutions are disclosed herein that help to manage battery usage and extend battery life in order to increase efficiency and throughput.

SUMMARY

An aspect of this application is to advance the art of medical digital radiography and to address, in whole or in part, at least the foregoing and other deficiencies of the related art. It is another aspect of this application to provide in whole or in part, at least the advantages described herein. For example, certain exemplary embodiments of the application address the need to provide automated battery power management in order to reduce downtime and increase productivity of the mobile radiography system.

A power consumption rate of a battery is monitored and is recorded as a battery power consumption profile associated with a plurality of daily time periods for the battery. Electric circuits connected to the battery are activated during high battery power consumption rate time periods and deactivated during low battery power consumption rate time periods. A stored control program is executable by a processor to control the automatic power downs and power ups.

In one embodiment, a mobile digital radiography system has a wheeled base with a transport drive system for driving the wheels. An x-ray is attached to the wheeled base using a column. An electronic control system receives operator input to selectively operate the radiography system. A battery provides power to the x-ray source, the transport drive system, and the electronic control system. A processing system records power demands of the portions of the mobile digital radiography system, including daily time periods wherein the power demands are below a threshold. A stored control program automatically powers down a selected portion during the recorded time periods when the power demands are below threshold.

In one embodiment, a method includes monitoring battery power consumption in a battery according to a daily time period. The battery power consumption is stored as a profile to identify a battery power consumption rate associated with the daily time period. Electric circuits connected to the battery are activated during daily time periods associated with the high battery power consumption, and are deactivated during a daily time period associated with a low battery power consumption.

In one embodiment, a portable digital radiography detector includes a plurality of photosensitive cells arranged in a two dimensional array for capturing digital radiographic images. An electronic control system communicates with the photosensitive cells to control activation thereof. A battery assembly provides power to the photosensitive cells, the electronic control system, and the control interface. A processing system records time periods wherein the power demands of the detector portions are less than a preset threshold. A stored control program automatically powers down one or more of the detector portions daily during the recorded time periods when the power demands are less than the preset threshold.

In one embodiment, a mobile digital radiography system includes a wheeled base with a transport drive system. An x-ray assembly includes an x-ray source and a support column attached to the wheeled base. An electronic control system receives operator input to selectively operate the transport drive system and the x-ray source. A battery provides power to the x-ray source, the transport drive system, and the electronic control system. A processing system records power demands including recording daily time periods wherein the power demands of the portions are below a threshold. A stored control program automatically powers down the portions of the radiography system during the recorded time periods.

In one embodiment, a method includes monitoring a power consumption rate of a battery and associating the consumption rates with daily time periods. These are recorded as a battery power consumption profile. Thereafter, electric circuits connected to the battery can be activated during a daily time period associated with a high battery power consumption rate as indicated by the battery power consumption profile and deactivating the electric circuits connected to the battery during low battery power consumption rate time periods as indicated by the battery power consumption profile.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

A detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DESCRIPTION OF EXEMPLARY EMBODIMENTS

In the context of the present disclosure, the phrase "in signal communication" indicates that two or more devices and/or components are capable of communicating with each other via signals that travel over some type of signal path. Signal communication may be wired or wireless. The signals may be digital signals used for communication and data, or energy signals such as for power transmission. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

An aspect of battery efficiency for many types of batteries, including the lead-acid batteries common to portable radiography equipment, relates to the power consumption profile of the powered equipment. In general, batteries run most efficiently when handling load levels that are fairly constant. Longest battery life is generally observed where current drain is relatively consistent during use, without pronounced variation or repeated, rapid transitions in cycling between high and low output levels.

Mobile x-ray systems, as described in the background section, are often used in environments where fairly routine schedules are followed. In hospital environments, for example, these systems may be regularly moved from one site to another, following patterns of transport and use that can be relatively consistent in terms of time scheduling, sequence of operations, hospital wing or other location, number of patients imaged, imaging time per patient, time to travel between patients, and the like. Correspondingly, battery power usage, varying in relation to the operations and functions performed, follows schedule patterns. Embodiments of the present disclosure take advantage of these patterns to define and refine corresponding system response for battery power management. By tracking, monitoring and recording battery power consumption patterns applicable to the mobile radiography system as a whole, or its components and sub-systems individually, at a particular site, control logic for the mobile radiography system can schedule power distribution, and control activation and/or deactivation of selected electric circuits connected to the battery for selected functions during high and/or low power consumption times of day in order to achieve a more efficient use of battery power.

Figure 1:
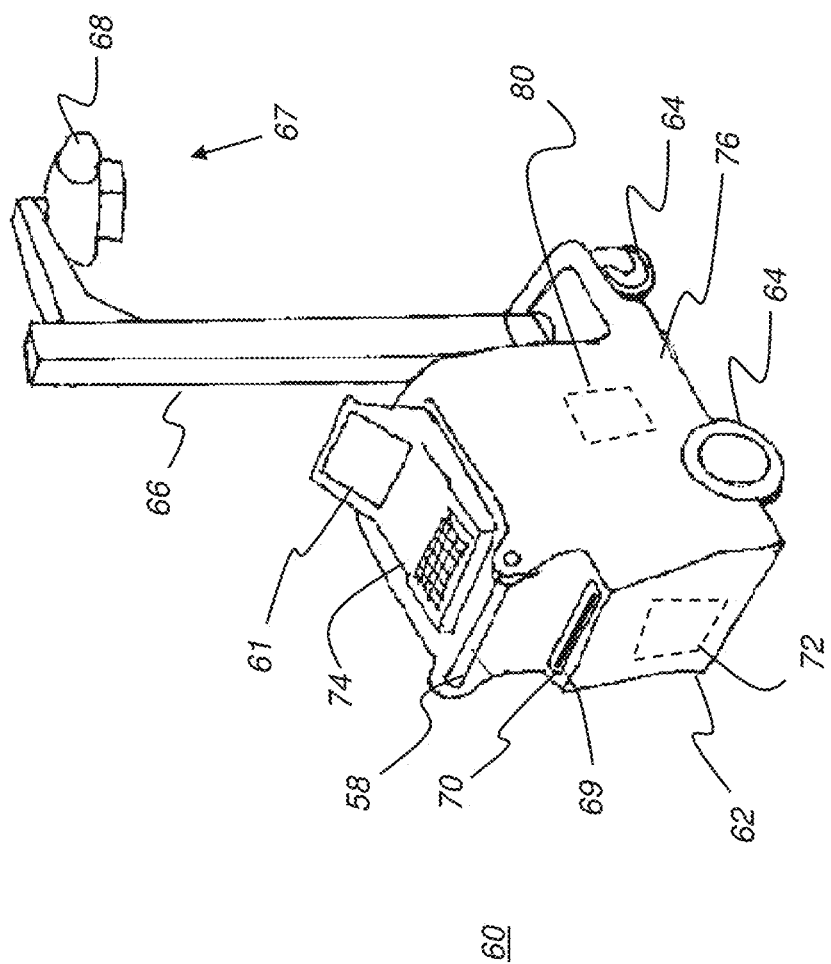
FIG. 1 is a perspective view of a mobile radiography system.
Figure 2:
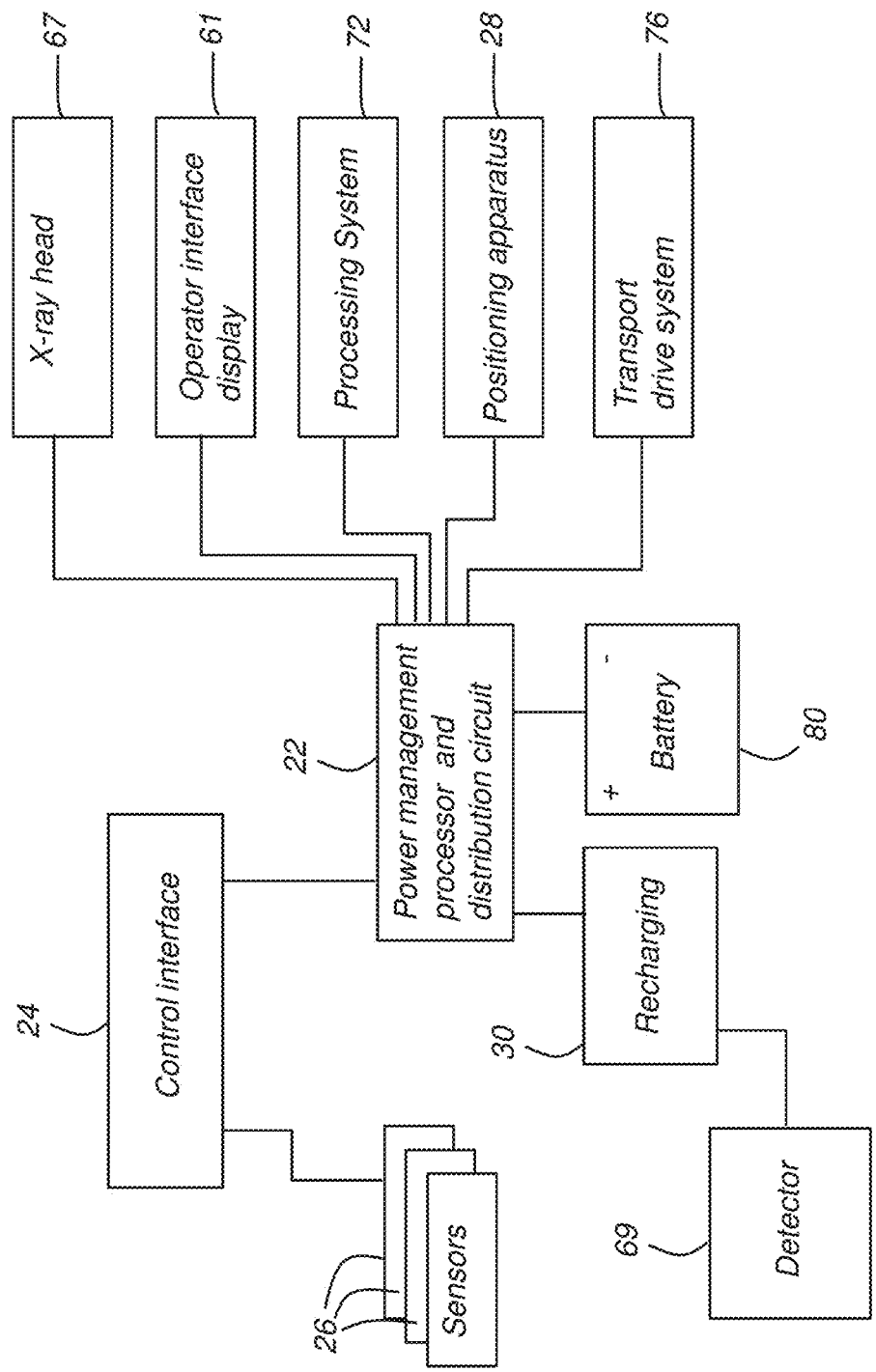
FIG. 2 is a schematic diagram of a power distribution mapping according to an embodiment of the present disclosure.

FIG. 2 is a schematic diagram of an exemplary power distribution scheme for the mobile radiography system 60 of FIG. 1. Power from the battery 80 is distributed and managed using a power management processor and distribution circuit 22, which may include a dedicated processor separate from the processing system 72 or it may be part of a more comprehensive control function provided by processing system 72.

The various sub-systems of mobile radiography system 60 shown in the schematic diagram of FIG. 2 obtain and use battery power at varying levels during normal operation. The x-ray head 67 includes x-ray source 68 and sub-systems for generating x-rays, such as an x-ray generator, as well as supporting subsystems for setup and control, such as a collimator light, for example. A control interface 24 requires power for operator interface functions provided on display 61 or as a separate console. Processing system 72 can be considered another power consumer with regard to power distribution. Positioning apparatus 28 can include motors, sensors, and other components used during setup and positioning of the mobile radiography system 60, including positioning of the x-ray head 67. Transport drive system 76 can include various motors and actuators for moving the mobile radiography system 60 between patient imaging sites. A recharging unit 30 can serve a number of functions, including controlling recharging of the battery 80 and recharging of a DR detector 69 inserted in the detector slot 70. Various sensors 26 can be powered throughout the mobile radiography system 60, which sensors 26 may be used for sensing position, movement and equipment status. A number of other components, including actuators, interlocks, lighting systems, audio and alarm apparatus, for example, can also be provided as parts of mobile radiography system 60 that require some amount of battery power for operation.

Power management processor 22 can be set up to use various thresholds for determining aspects of power demands and controlling power usage. Thresholds may be set by an operator of the mobile radiography system 60 under program control. Digital radiography DR detector 69 is typically configured with a two dimensional array of photosensitive cells used to capture digital radiographic images. The DR detector 69 typically requires an electronic control system configured to communicate with the photosensitive cells for controlling activation of the photosensitive cells. DR detector 69 can also have an on-board battery assembly that provides power to portions of the DR detector 69, including the photosensitive cells and the electronic control system. A processing system within DR detector 69 can be configured to record power demands of one or more portions of the DR detector 69 as described herein, including recording daily time periods wherein the power demands of the one or more portions of the DR detector 69 may be more or less than one or more preset thresholds. A stored control program executable by the processing system of the DR detector 69 can be configured to automatically power down a selected one or more portions of the DR detector 69 daily during the recorded time periods wherein the power demands are less than the one or more preset thresholds. Similarly, a stored control program executable by the processing system of the DR detector 69 can be configured to automatically power up a selected one or more portions of the DR detector 69 daily during the recorded time periods wherein the power demands are greater than the preset thresholds. The DR detector 69 may also include a wireless transmitter to transmit captured radiographic images and a circuit to detect a strength of the wireless communication channel.

Figure 3:
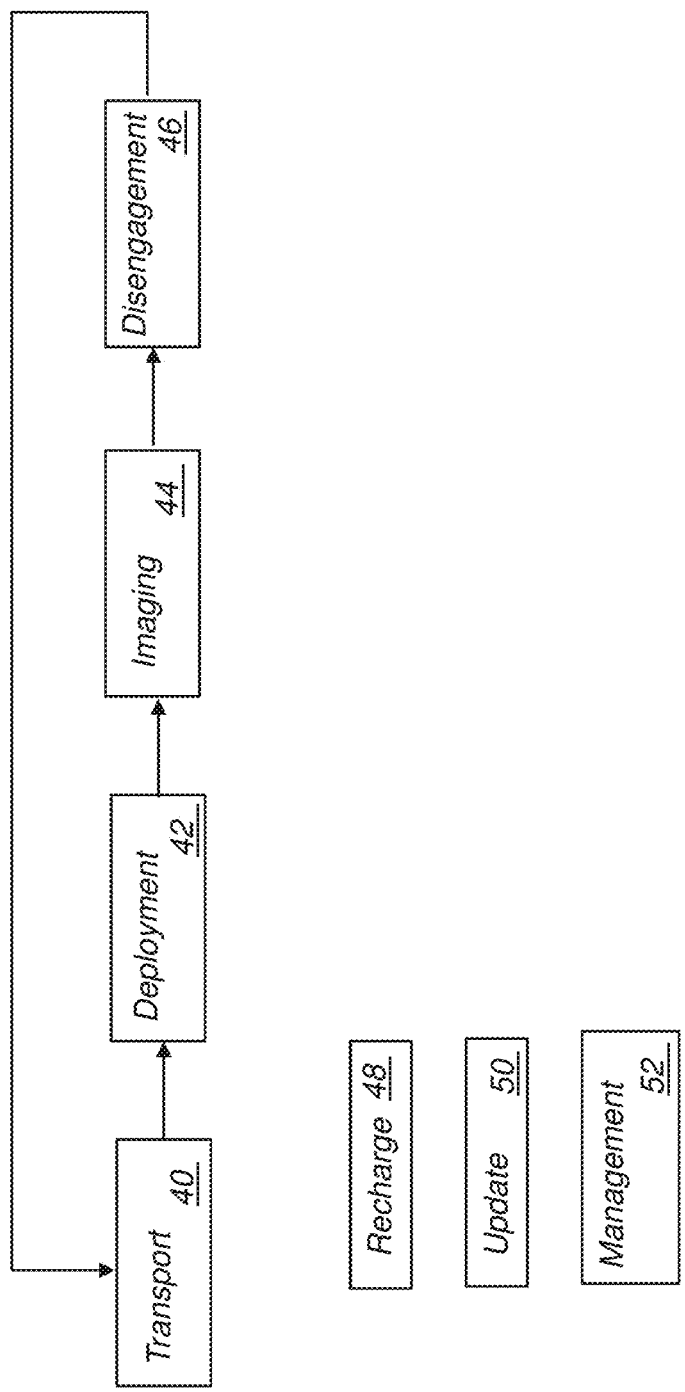
FIG. 3 is a flow diagram of an exemplary functional sequence with phases of operation executed by a mobile radiography system.

While numerous workflow patterns, and thereby power demand patterns, are possible with respect to the mobile radiography system 60, there are general patterns that are likely to be followed for a sequence of operations that affect battery usage. By way of example, the workflow diagram of FIG. 3 shows an exemplary functional sequence with phases of operation executed by a mobile radiography system 60 at a typical site. In a transport phase 40, mobile radiography system 60 is moved from one location in a hospital, clinic, or other site, to another location using the transport drive system 76, for example. In a deployment phase 42, the mobile radiography system 60 is set up by an operator for an imaging session at a particular location, such as at a patient bedside. The deployment phase 42 may include DR detector 69 being removed from detector slot 70 (FIG. 1) and positioned behind a patient. In an imaging phase 44, the x-ray source 68 may be powered up and fired while the DR detector 69 captures digital image data, processes the digital image data and wirelessly transmits the processed digital image. Actuation energy is provided to the x-ray generator components of x-ray head 67. In a disengagement phase 46, the mobile radiography system 60 may be powered down and reconfigured into a stowed position to allow transport to the next location for imaging.

FIG. 3 also shows a number of functional phases that can be independent of the imaging workflow sequence just described with respect to phases 40 through 46. A recharge phase 48 may be executed in order to recharge the internal battery 80, for systems where the battery 80 is not removed, separately charged and replaced. An update phase 50 may execute periodically for software updates, and uploading or downloading of schedule information or other data. Update phase 50 can also be used for dedicated transmission time of acquired image content or transfer of patient data to a networked server or other external processing device, for example. A management phase 52 can include monitoring and control of various processing functions, including operator and equipment management as well as battery use management functions.

Figure 4:
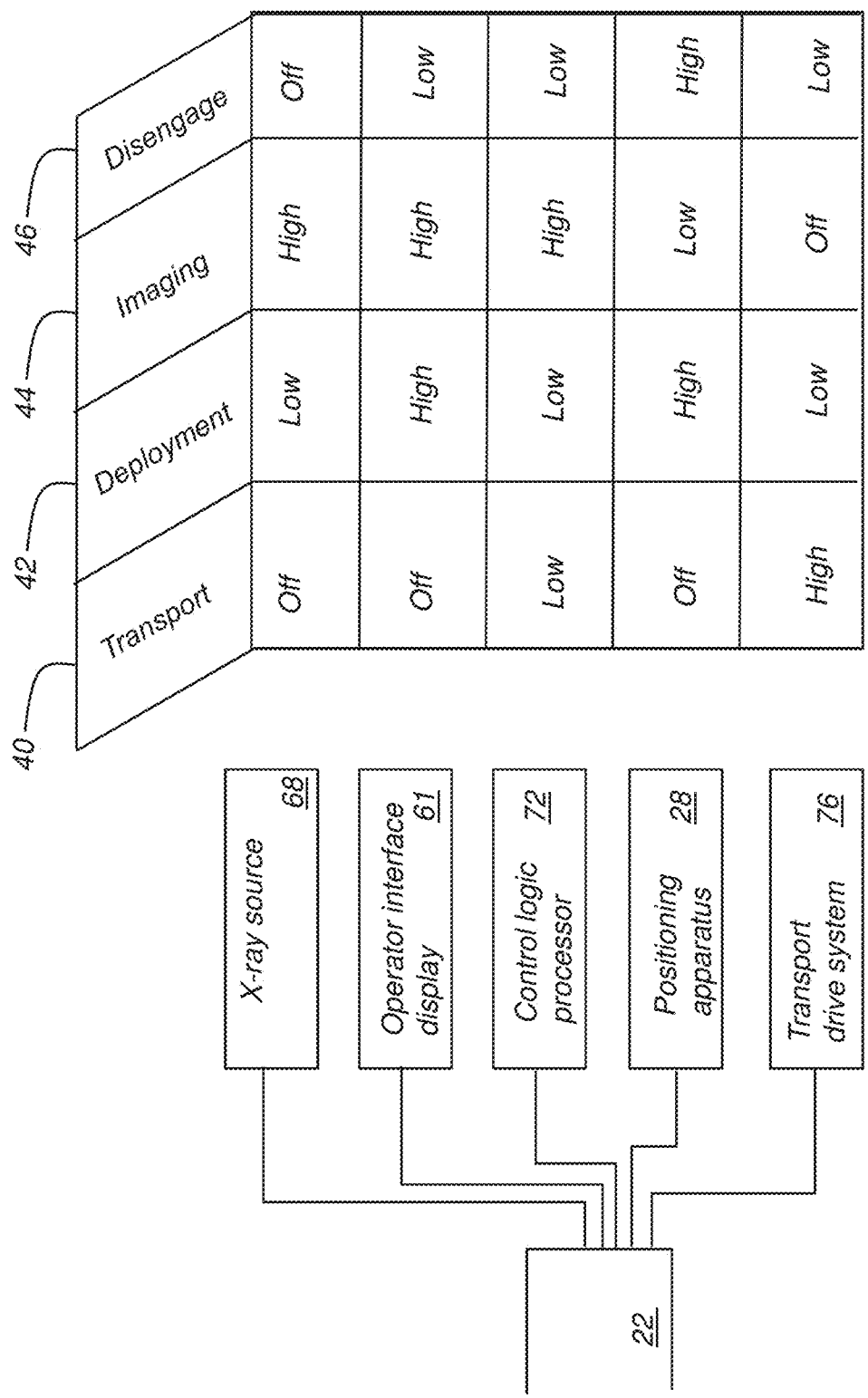
FIG. 4 is a tabular diagram that relates relative power consumption levels to sub-systems of a mobile radiography system during different phases of operation.

It can be readily appreciated that the various phases outlined in FIG. 3 require different levels of battery power for the various sub-systems identified in the mapping of FIG. 2. By way of example, the table of FIG. 4 illustrates power consumption levels corresponding to sub-systems of a mobile radiography system 60 during different phases of operation. During imaging phase 44, for example, there is no power demand from the transport drive system 76, as indicated by the designation "Off", because the transport components are effectively turned off during patient exposure. During deployment phase 42, there may be some need for power to transport drive system 76, such as to provide incremental movement of the mobile radiography system 60 near to the patient; however, this power requirement is typically a reduced power requirement, as indicated by the designation "Low", and would require only short bursts of power to the transport drive system 76. During a transport phase 40, the transport drive system 76 is normally fully engaged and demands a standard level usage power supply, as indicated by the designation "High". Thus, the designations "Off", "Low", and "High" may be stored as text labels within the processing system 72 of the mobile radiography system 60, or they may correspond to stored programmed numerical voltage levels in the mobile radiography system

60. In either case, these designations may be correlated with times of day, and may serve to identify thresholds that are used by the processing system 72 for determining power usage patterns, as described herein.

Figure 5:
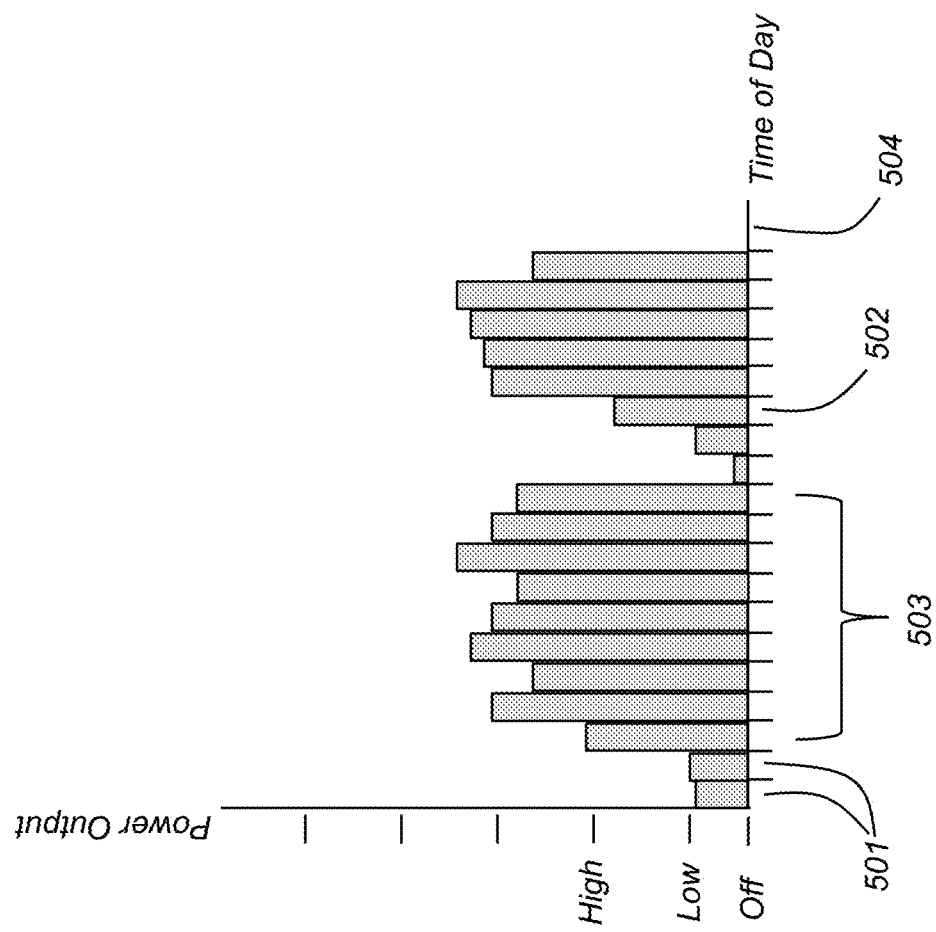
FIG. 5 is an exemplary graph of power consumption rates for a battery, a sub-system, or detector used with the mobile radiography system over time.

In many environments, varying battery power requirements for the different sub-systems of mobile radiography system 60 also depend on scheduling and timing patterns. The bar graph of FIG. 5 shows exemplary battery power output or power consumption profile for an exemplary typical sub-system described herein of the mobile radiography system 60, varying over time of day. (Time units and output power units are arbitrary in the representation shown in FIG. 5.) It can be appreciated that the schedule patterns that apply to any particular medical facility can be correlated to a number of use factors, such as the type of site, number of technicians, types of patients served, work shift assignments, DR detector types used, etc.

According to an embodiment of the present disclosure, power management processor 22 continually monitors battery usage during various operations or time of day, or both, and generates a profile of battery power consumption related to schedule and various use factors, including location, operator, and type of DR detector 69 in use, for example. A stored battery power consumption profile recorded by processor 22, or the processor of processing system 72 (FIG. 1) can generate the two dimensional power output schedule graphically shown in FIG. 5 (power output vs. time of day) for each subsystem, as well as related data on location, detector type, and other categories described herein. If other categories of usage patterns are monitored and recorded, the generated table may be a multi dimensional table having many patterns recorded. Such a multi dimensional table may provide a control schedule with a greater resolution for fine tuning power usage by powering down and powering up components of the mobile radiography system 60 more frequently. Using an exemplary recorded battery power consumption profile, processor 22 can determine, for example, that display 61 can be turned off or put into a low-power or standby mode because stored accumulated power usage data indicates that these two sub-systems are rarely, if ever, powered on together. Conversely, stored accumulated power usage data may indicate that when the operator display 61 is operative, it may be suitable to reduce power to the drive transport system 76 and to provide various positioning actuators with standby power. Power to various subsystems of the mobile radiography system 60 can thus be selectively adjusted according to the stored profile. The profile can be continually updated and averaged over time, allowing for changes in scheduling and system utilization. Such a program may be configured to allow an operator to delete a stored power usage profile in order to re-accumulate power usage data. This re-accumulation may be useful if the mobile radiography system 60 is assigned to a different department of a medical facility where different power usage patterns are expected.

Equipment location is one factor that can be indicative of different expectations for usage patterns. Global Positioning System (GPS) logic or other location data can be used to relate schedule characteristics for particular locations, such as specific wards of a hospital, for example. The GPS information can be provided from mobile radiography system 60 by a sensor mounted within the frame 62 or can alternately be obtained from a GPS sensor within the DR detector 69. Thus, a power usage profile program may be configured to automatically delete a stored power usage profile in order to re-accumulate power usage data when a significant GPS location difference is detected.

It can be appreciated that improved power management can be provided by selectively energizing or de-energizing various sub-system components during different detected phases of operation or times of day. In particular, high demand components such as motors, radiation generators, and other components can be controlled to have different active ("High"), standby ("Low"), "sleep" ("Off"), or de-energized modes depending on the phase, scheduling, or time of day that is followed. With more effective battery power management, system utilization can be improved, along with battery life and system up-time.

The exemplary structure and functional patterns shown in FIGS. 2, 3, 4, and 5 show various types of information that can be tracked and used as input to learning software that can support efficient battery power management. Software providing neural network learning, applying variously termed "fuzzy logic" or artificial intelligence, can be programmed to store and analyze scheduling and usage patterns for an individual system or group of systems and to better manage resources such as battery power.

As noted previously with respect to FIG. 2, various types of sensors 26 can be distributed throughout the mobile radiography system 60. For example, wireless DR detector 69 may employ some type of accelerometer and/or gyroscope for various functions related to imaging and positioning. In addition, the base frame 62 of the mobile radiography system 60 can include various sensors, including accelerometers and other motion and positioning sensors. Global Positioning Systems (GPS) logic can also be available, using a suitable range of available methods and devices.

Learning software, programmed using neural network or other learning logic approaches, can be applied to the task of collecting scheduling and usage patterns data from a mobile radiography system 60 in order to learn and anticipate likely battery power distribution and demand. Once the workflow patterns have been learned, peak and low power demand times can be learned, recorded and, thereby, automatically optimized to schedule power on, standby, and power off times of the mobile radiography system 60, the DR detector 69, and other components, as described herein, without compromising system responsiveness and overall performance. As shown in FIG. 5, a particular component of the mobile radiography system 60 having the power usage pattern depicted therein, may be programmed to enter a first "low power" state, e.g., a sleep state, during time of day periods 501, a second but higher "medium power" standby state during time of day period 502, and a third even higher "high power" active state during time of day periods 503. A fourth "lowest power" off state may be programmed for time of day period 504. Thus, over a period of time, power consumption of the DR detector 69 or other components of the mobile radiography system 60 can be "learned". Peak power periods can then be fine tuned, such as by automatically deferring non-essential power functions for off-peak power periods. Non-essential power functions can include self-diagnostics, transferring files/images, software downloads.

In order to better conserve power, the DR detector 69 can also be automatically put into a low power sleep state when not typically in use, such as during detected periods that are typically transport phases or idle phases. In addition to more efficient power distribution within the device, the usage information that is obtained can have other benefits. For example, a hospital administrator may be able to discern when and where a DR detector 69 is most often subjected to motion or handling and can use this information to improve workflow scheduling, thus helping to minimize or eliminate shock or drop damage to the equipment.

For example, motion sensing data from accelerometers in the DR detector 69 or in the radiography cart may indicate a recurrent idle period during a workshift, such as during a lunch break or other periodic event. The system could then automatically power down various non-essential functions of the mobile radiography system 60/DR detector 69 when parked, automatically restoring power for an active state at the end of the hour. This off-peak power time could then be used to perform non-essential power functions, such as system software update or maintenance/usage log transfer, to minimize peak power consumption.

As another example, usage data can indicate that a system is driven for 15 minutes continuously each morning at 8 AM, traveling from the ICU to the ER. This can be information obtained by monitoring accelerometers contained in the mobile radiography system 60, including devices contained within associated DR detector 69. Alternately, information can be acquired by recording activity of various actuators. For example, during this period only the transport drive system is active and no independent DR detector 69 movement is recorded. Since only the transport drive system is required, all other component power functions can be automatically shut down or put into a sleep state during this recurring transport period. At or towards the end of transport, systems can then be automatically powered on.

As yet another example, the mobile radiography system 60 can learn that between 2 and 5 PM, the DR detector 69 is moved from the x-ray cart to a fixed DR room. The mobile radiography system 60 can then be automatically shut down or put into a low power sleep state, to be re-energized just prior to the scheduled time for continuing mobile rounds. This approach could thus help to minimize or eliminate the time needed for cart battery 80 recharge between rounds.

Figure 6:
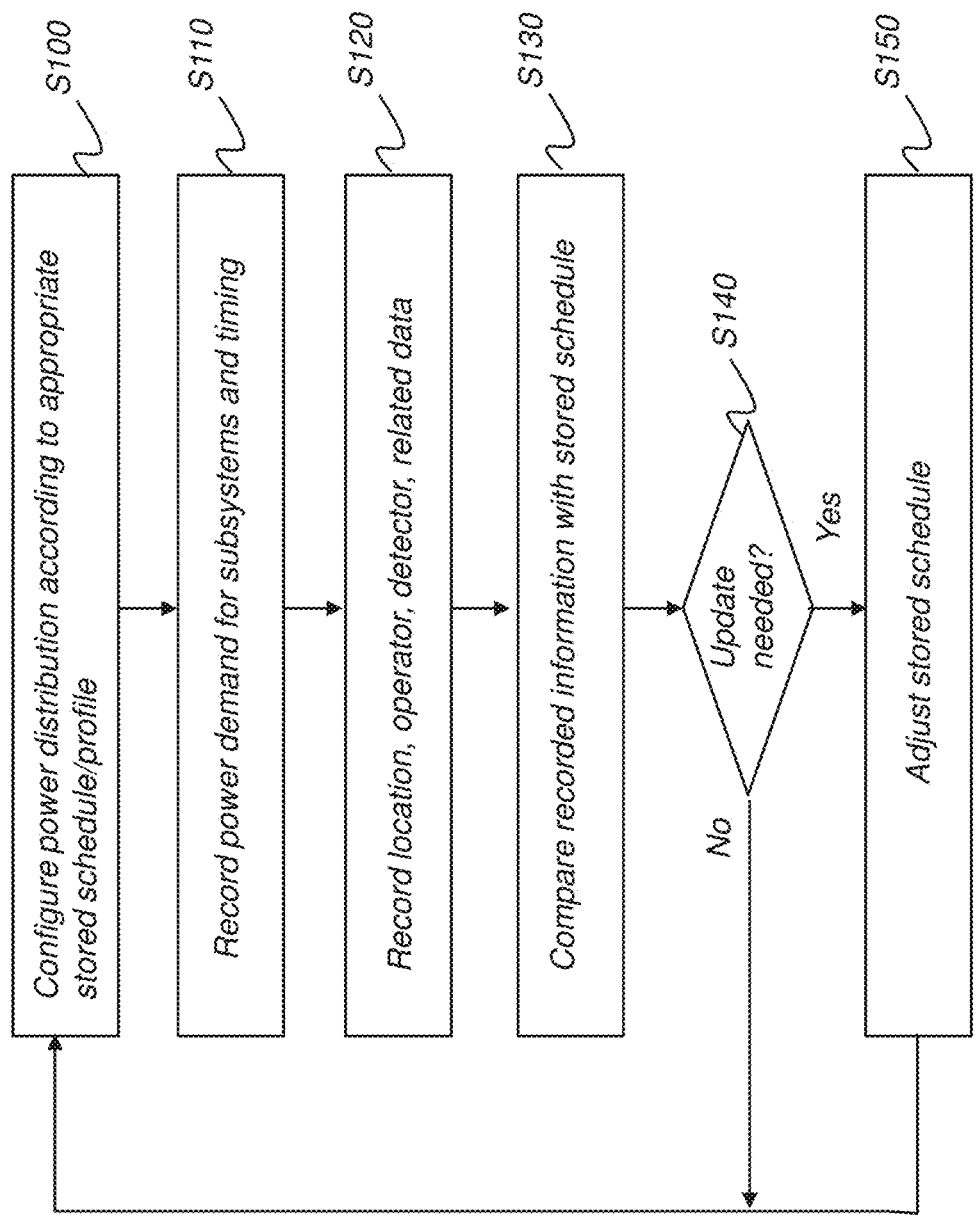
FIG. 6 is a logic flow diagram for operation, monitoring, and adjustment of a power distribution for the mobile radiography system according to an embodiment of the present disclosure.

The logic flow diagram of FIG. 6 shows a sequence for operation, monitoring, and adjustment of power distribution response for the mobile radiography system 60 according to an embodiment of the present disclosure. At a known power up time or initiation of a scheduled work shift, for example, a programmed configuration step S100 provides initial configuration of the mobile radiography system 60 according to learned usage patterns, stored as a schedule or profile for the mobile radiography system 60. As the mobile radiography system 60 is used, an operations recording step S110 continually records the sequence of operations and compares power distribution requirements with stored power demand data. A factors recording step S120 records factors related to system usage, such as operator ID, DR detector 69 type(s) used or employed, location, day of the week, time of day, and other factors affecting usage. A comparison step S130 compares the usage information related to recent activity that is currently being recorded with previously stored schedule data. A decision step S140 determines whether or not changes in the stored data justify an update, such as by an average, a weighted average, or other statistical measure of centrality, of the stored schedule. If no update is needed, operation continues using response information stored in the current profile. If update is advised, an update step S150 executes, adjusting the stored schedule.

Figure 7:
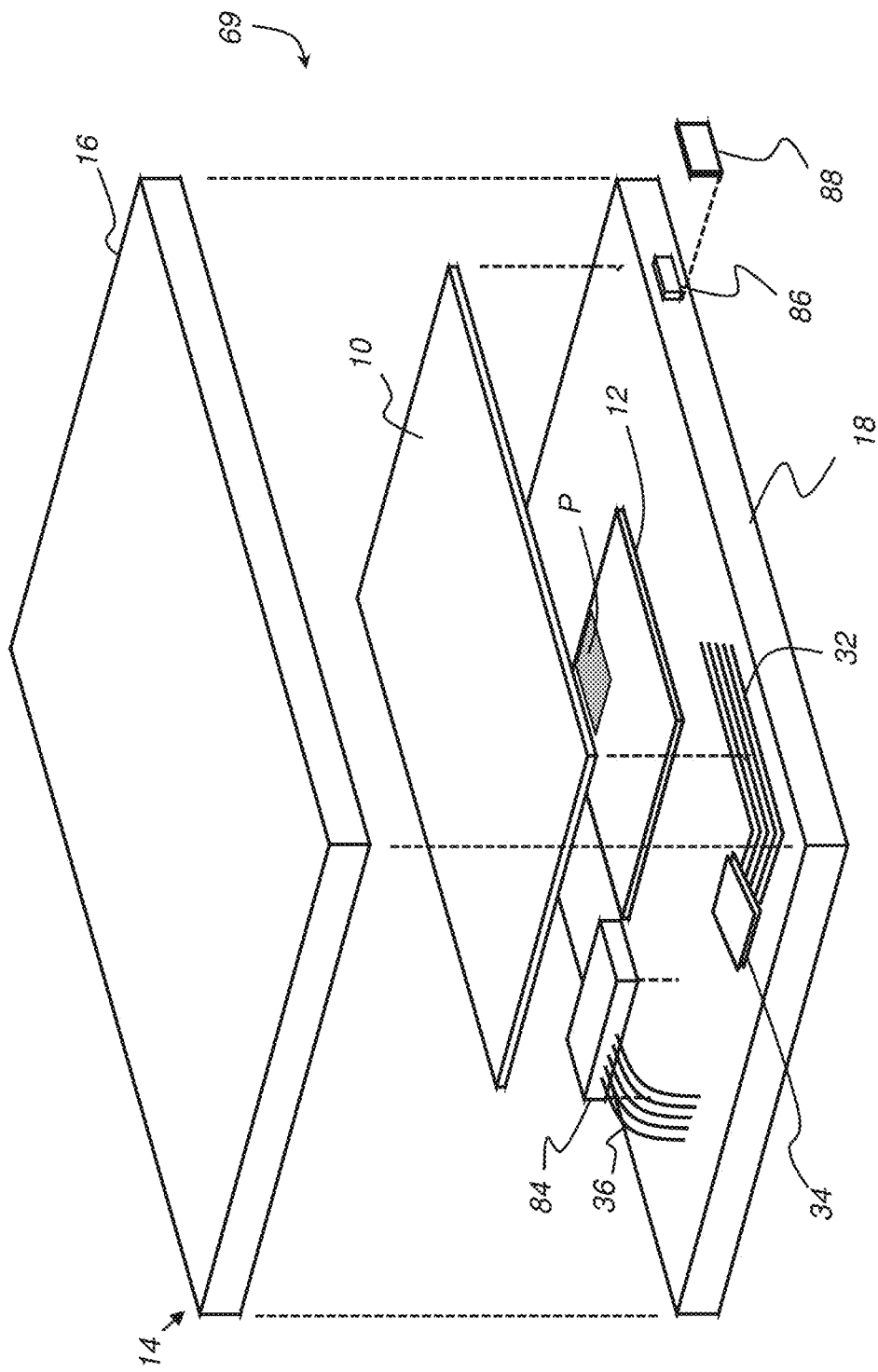
FIG. 7 is an exploded view that shows, schematically, some of the electrically active internal components of a DR detector used with a mobile radiography system.

An embodiment of the present disclosure can similarly be used for improved power management for DR detector 69. The exploded view of FIG. 7 shows, in simplified form, some of the electrically active internal components of DR detector 69 that are protected within an enclosure or housing 14 formed using multiple parts, including top and bottom covers 16 and 18. A detector imaging array 10 includes a scintillator layer that provides a recording medium that generates output light energy when energized according to x-ray exposure and electromagnetic radiation sensitive elements disposed in a two-dimensional array for capturing image signals from received radiation to provide data for imaging pixels. A circuit board 12 provides a logic processor with supporting control electronics components for image data acquisition and wireless transmission to an external host system. Circuit board 12 includes a detector element to initiate a start of exposure and a termination of the exposure. A battery 84 provides power, acting as the voltage source for detector operations. A port 86 extending through bottom cover 18 is provided to allow electrical connection for receiving and transmitting data, and/or receiving power such as from a voltage supply. The port may have an optional cover plate or sealing cap 88, which may be a rubber seal or other liquid-proofing material. In addition to the illustrated components, a number of interconnecting cables, supporting fasteners, cushioning materials, connectors, and other elements may be used for packaging and protecting the detector circuitry. An optional antenna 32 and transmitter 34 for wireless communication may alternately be provided, with antenna 32 extending within the housing 14. Top and bottom housing covers 16 and 18 may be fastened together along a mating surface. One or more cables 36, such as multi-wire flexible cables, may also be included within housing 14 for interconnection between components. The rechargeable battery 84 for the wireless detector is typically a Lithium-ion battery (LIB) battery pack, often used for portable electronics devices. Alternately, a storage capacitor can be used for providing portable device power.

Within detector, a processor P on circuit board 12 can be configured to record power demands of one or more portions of the DR detector 69, including recording daily time periods wherein power demands of one or more portions of the DR detector 69 are less than one or more preset thresholds. A stored control program, executable by the processing system, can be configured to automatically power down to a first power level selected portions of the DR detector 69 daily during the recorded time periods wherein the power demands are less than a first preset threshold. The stored control program can be configured to automatically power down to a second power level selected portions of the DR detector 69 daily during the recorded time periods wherein the power demands are less than a second preset threshold. The on-board processing system can also be configured to record daily time periods wherein the power demands of the one or more of said portions are greater than the first or second preset thresholds. A stored control program can be executable by the processor to automatically power up to selected power levels one or more selected portions of the DR detector 69 daily during the recorded time periods wherein the power demands are greater than the first or second preset thresholds.

Processor circuitry on DR detector 69 can alternately include a circuit to detect the strength of a wireless communication channel, with the stored control program executable by the processing system configured to transmit captured radiographic images only if the detected strength of the wireless communication channel exceeds a preset threshold. This detection method minimizes power drain on the battery so that captured digital images may be transmitted using an optimal amount of power.

The training function described herein can be ongoing, repeated one or more times during normal use of the equipment. Repeating this training sequence during imaging with actual practitioners and patients can help to improve overall system response and allow adaptation of equipment to changes in environment and usage.

Consistent with one embodiment, the present invention utilizes a computer program with stored instructions that control system functions for sensor data acquisition and processing. As can be appreciated by those skilled in the data processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various data manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the sensor and signal processing arts. Additional aspects of such algorithms and systems, and hardware and/or software for producing and otherwise processing the acquired data or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. In addition, while a feature(s) of the invention can have been disclosed with respect to only one of several implementations/embodiments, such feature can be combined with one or more other features of other implementations/embodiments as can be desired and/or advantageous for any given or identifiable function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed:

1. A mobile digital radiography system comprising:
a wheeled base including a transport drive system for transporting the mobile digital radiography system;
an x-ray assembly comprising an x-ray source and a support column attached to the wheeled base;
an electronic control system configured to receive operator input to selectively operate the radiography system, including the transport drive system and the x-ray source;
a battery to provide power to portions of the mobile digital radiography system, said portions including the x-ray source, the transport drive system, and the electronic control system;
a processing system configured to record specific hourly daily times of day when power demands of one or more of said portions of the mobile digital radiography system are less than a first preset threshold; and
a stored control program executable by the processing system to automatically power down a selected one or more of said portions of the radiography system daily during the specific hourly daily times of day as recorded by the processing system and to automatically restore power at an end of a specified hour.

2. The system of claim 1, further comprising the processing system configured to record daily times of day when the power demands of the one or more of said portions are greater than a second preset threshold; and
a stored control program executable by the processing system to automatically power up a selected one or more of said portions of the radiography system daily during the recorded daily times of day when the power demands are greater than the second preset threshold.

3. The system of claim 1, wherein the processing system is further configured to record location information related to the power demands.

4. The system of claim 2, further comprising:
a collimator light in the x-ray assembly;
a drive wheel and a drive motor for driving the drive wheel; and
an electronic monitor comprising a display, wherein the portions of the digital radiography system configured to be automatically powered up or powered down by the stored control program include the collimator light, the drive motor, and the electronic monitor.

5. The system of claim 3, further comprising a global positioning system for obtaining the location information.

6. A method comprising:
monitoring a battery power consumption rate of a battery, including associating the monitored battery power consumption rate with specified hourly times of day;
recording a battery power consumption profile of the battery, wherein the battery power consumption profile identifies a battery power consumption rate associated with the specified hourly times of day; and
activating electric circuits connected to the battery during the specified hourly times of day associated with a high battery power consumption rate as indicated by the battery power consumption profile and deactivating the electric circuits connected to the battery during the specified hourly times a daily time of day associated with a low battery power consumption rate as indicated by the battery power consumption profile.

7. The method of claim 6, further comprising averaging the battery power consumption rate associated with the specified hourly times of day over a plurality of days.

8. The method of claim 6, further comprising providing a mobile radiography apparatus having a transport drive system, and wherein the step of activating and deactivating comprises activating and deactivating the transport drive system of the mobile radiography apparatus.

9. A mobile digital radiography system comprising:
a wheeled base including a transport drive system for transporting the mobile digital radiography system;
an x-ray assembly comprising: an x-ray source, and a support arm attached to the x-ray source and to the wheeled base;
an electronic control system configured to receive operator input to selectively operate the mobile digital radiography system, including the transport drive system and the x-ray source;
a battery to provide power to portions of the mobile digital radiography system, said portions including the x-ray source, the transport drive system, and the electronic control system;
a processing system configured to record specific hourly daily times of day when power demands of one or more of said portions of the mobile digital radiography system are greater than a first preset threshold; and
a first stored control program executable by the processing system to automatically power up a selected one or more of said portions of the radiography system daily during the recorded specific hourly daily times of day when the power demands are greater than the first preset threshold.

10. The system of claim 9, further comprising a second stored control program executable by the processing system to automatically power down a selected one or more of said portions of the radiography system daily during the recorded specific hourly daily times of day when the daily power demands are less than a second preset threshold.

11. The system of claim 9, wherein the processing system is further configured to record location information related to the specific hourly daily times of day when power demands are greater than the first preset threshold.

12. The system of claim 10, further comprising:
a collimator light in the x-ray assembly;
a drive wheel and a drive motor for driving the drive wheel; and
an electronic display electrically connected to the electronic control system,
wherein the portions of the mobile digital radiography system automatically powered up or powered down by the first and second stored control programs include the collimator light, the drive motor, and the electronic display.

13. The system of claim 11, further comprising a global positioning system for obtaining the location information.

* * * * *